(12) United States Patent
Frelich et al.

(10) Patent No.: US 11,794,145 B1
(45) Date of Patent: Oct. 24, 2023

(54) ATMOSPHERIC GREENHOUSE GAS REDUCTION USING PARTICLES

(71) Applicant: Nano BlueSkies Corp., Plymouth, MN (US)

(72) Inventors: Lee Frelich, Minneapolis, MN (US); John MacDonald, Plymouth, MN (US)

(73) Assignee: Nano BlueSkies Corp, Plymouth, MN (US)

( * ) Notice: Subject to any disclaimer, the term of this patent is extended or adjusted under 35 U.S.C. 154(b) by 1 day.

(21) Appl. No.: 17/486,992

(22) Filed: Sep. 28, 2021

Related U.S. Application Data

(60) Provisional application No. 63/090,984, filed on Oct. 13, 2020.

(51) Int. Cl.
| | | |
|---|---|---|
| *B01D 53/62* | (2006.01) | |
| *C12N 1/20* | (2006.01) | |
| *C12P 19/00* | (2006.01) | |
| *C12R 1/01* | (2006.01) | |

(52) U.S. Cl.
CPC .............. *B01D 53/62* (2013.01); *C12N 1/20* (2013.01); *C12P 19/00* (2013.01); *B01D 2257/504* (2013.01); *C12R 2001/01* (2021.05); *Y02P 20/151* (2015.11)

(58) Field of Classification Search
CPC .... B01D 53/62; B01D 2257/504; C12N 1/20; C12N 1/12; C12N 1/10; C12N 13/00; C12P 19/00; C12P 5/023; C12P 7/649; C12R 2001/01; Y02P 20/151; C12M 21/02; C12M 31/10; C12M 31/00; C12M 31/02; C12M 31/08; C12M 31/12; C12M 23/06; C12M 23/22; C12M 43/06; C12M 43/08; Y02E 50/13; Y02E 50/343; A01G 33/00; C02F 3/32
See application file for complete search history.

(56) References Cited

U.S. PATENT DOCUMENTS

| | | | | |
|---|---|---|---|---|
| 4,375,515 A | * | 3/1983 | Patel ................... | C12N 1/16 435/189 |
| 2011/0250659 A1 | * | 10/2011 | Roberts ................ | C12N 15/74 435/257.2 |
| 2012/0065439 A1 | * | 3/2012 | Siemer ................. | C12M 21/02 585/16 |
| 2015/0225271 A1 | * | 8/2015 | Fry ...................... | C12N 13/00 435/294.1 |

* cited by examiner

*Primary Examiner* — Michael L Hobbs
(74) *Attorney, Agent, or Firm* — Spencer Fane LLP

(57) ABSTRACT

An atmospheric greenhouse gas reduction system that includes greenhouse gas reduction particles having carbon dioxide conversion material that is capable of converting carbon dioxide in atmosphere into simple carbohydrates. The greenhouse gas reduction particles have a size of up to about 1,000 nanometers.

8 Claims, 1 Drawing Sheet

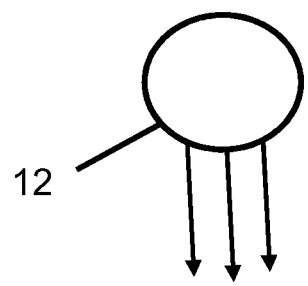
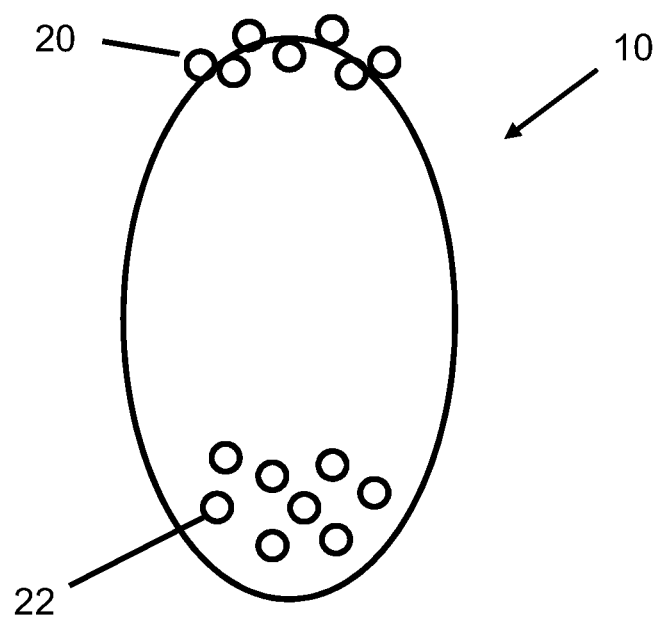

ATMOSPHERIC GREENHOUSE GAS REDUCTION USING PARTICLES

REFERENCE TO RELATED APPLICATION

This application claims priority to Provisional Applic. No. 63/090,984, filed on Oct. 13, 2020, the contents of which are incorporated herein by reference.

FIELD OF THE INVENTION

The invention relates generally to atmospheric greenhouse gas reduction. More particularly, the invention relates to atmospheric carbon dioxide and methane reduction using greenhouse gas reduction particles.

BACKGROUND OF THE INVENTION

It is well recognized that the level of carbon dioxide in the atmosphere is increasing from the activities of humans on the earth. It is also well recognized that the increased level of carbon dioxide in the atmosphere can lead to an increase in the temperature of the atmosphere.

A variety of techniques for carbon dioxide sequestration have been evaluated for reducing the level of atmospheric carbon dioxide. However, none of these techniques has proven to be viable for removing large amounts of carbon dioxide from the atmosphere.

It is also recognized that certain other chemicals, which are classified as greenhouse gases, negatively impact the typical passage of heat through the atmosphere. An example of one such greenhouse gas is methane.

SUMMARY OF THE INVENTION

An embodiment of the invention is directed to an atmospheric greenhouse gas reduction system including greenhouse gas reduction particles having carbon dioxide conversion material that is capable of converting carbon dioxide in atmosphere into simple carbohydrates. The greenhouse gas reduction particles have a size of up to about 1,000 nanometers.

Another embodiment of the invention is directed to an atmospheric greenhouse gas reduction method. Greenhouse gas reduction particles are formed having carbon dioxide conversion material. The greenhouse gas reduction particles are inoculated into the atmosphere. After inoculation, a region of the greenhouse gas reduction particles in which the carbon dioxide conversion material is located is oriented away from earth. The carbon dioxide conversion material converts carbon dioxide in the atmosphere into simple carbohydrates.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

The FIGURE is a depiction of a particle that is used in conjunction with an embodiment of the invention.

DETAILED DESCRIPTION OF THE INVENTION

An embodiment of this invention relates to the use of airborne particles such as illustrated at 10 in the FIGURE to reduce greenhouse gases in the atmosphere. An example of two greenhouse gases that the invention may be used to remove from the atmosphere are carbon dioxide and methane.

The greenhouse gas reduction particles 10 may include more than one region where each region performs a different function in the removal of carbon dioxide and/or other materials such as methane from the atmosphere.

As used herein, the greenhouse gas reduction particles 10 may have a diameter of up to about 1,000 nanometers. In other embodiments, the greenhouse gas reduction particles 10 have a diameter of between about 1 nanometer and about 100 nanometers.

Nano-bacteria generally has a size of between about 50 nanometers and about 400 nanometers. Photosynthetic bacteria such as *Prochlorococcus* generally have a size of between about 500 nanometers and about 800 nanometers.

It is also possible to utilize the concepts of the invention in conjunction with microparticles, which are generally viewed as having a size that is between about 1 micrometer and about 100 micrometers.

A first region 20 of the greenhouse gas reduction particles 10 may include nano-chloroplasts. The nano-chloroplasts thereby utilize a photosynthesis process in which the atmospheric carbon dioxide is converted to simple carbohydrates. This process may also include the formation of oxygen molecules. The nano-chloroplasts may be selected to remain active in the ambient conditions in which the greenhouse gas reduction particles 10 are intended to be used.

For situations where the greenhouse gas reduction particles 10 are intended to be deployed into the middle or upper atmosphere, the nano-chloroplasts should remain active into relatively low temperatures that are typically experienced in the upper atmosphere.

As used herein, upper atmosphere means a portion of the atmosphere that is at an altitude of more that is at least 50 kilometers above the earth surface. The upper atmosphere is generally viewed as extending to a distance of about 10,000 kilometers about the earth surface.

The concepts of the invention may also be used for removal of greenhouse gases from the lower atmosphere and the middle atmosphere. The primary advantage of using greater altitude is that it causes the greenhouse gas reduction particles to remain airborne for a longer period of time.

In certain embodiments, the greenhouse gas reduction particles 10 are configured so that when airborne, the first region 20 is oriented away from the ground and towards the sun. Orienting the greenhouse gas reduction particles 10 with the first region 20 oriented upwards enables the nano-chloroplasts to receive energy from the sun that is subsequently used in photosynthesis. The photosynthesis captures carbon dioxide from the atmosphere and thereby sequesters the carbon dioxide.

A variety of techniques may be used to cause the first region 20 to be oriented away from the ground. An example of one such technique that may cause the greenhouse gas reduction particles 10 to be oriented so that the first region 20 is oriented away from the ground is by making the first region 20 less dense than other region(s) in the greenhouse gas reduction particles 10.

In certain embodiments, the nano-chloroplasts may be provided on the surface of the greenhouse gas reduction particles 10. An advantage of providing the nano-chloroplasts on the surface of the greenhouse gas reduction particles 10 is that the surface of the greenhouse gas reduction particles 10 may permit the simple carbohydrates to separate from the greenhouse gas reduction particles 10. Using such a process, the greenhouse gas reduction particles 10 do not increase in weight as the simple carbohydrates are formed because such additional weight may reduce the potential of the greenhouse gas reduction particles 10 to remain airborne.

Alternatively, the greenhouse gas reduction particles 10 may become progressively heavier as the simple carbohydrates are produced and retained in the greenhouse gas reduction particles 10 such that eventually gravity causes the greenhouse gas reduction particles 10 to fall to the ground. A potential advantage of such a configuration is that the simple carbohydrates may be contained in the greenhouse gas reduction particles 10 to prevent or reduce the potential of negative effects being experienced in the areas in which the simple carbohydrate loaded greenhouse gas reduction particles 10 fall to the ground.

The nano-chloroplasts should be selected to perform in the conditions in which the greenhouse gas reduction particles 10 are intended to be used. For situations where the greenhouse gas reduction particles are intended to be deployed in the upper atmosphere, the nano-chloroplasts should remain active in the relatively low temperatures that are typically experienced in the upper atmosphere.

The photosynthesis may utilize water vapor that is present in the atmosphere. As such, the greenhouse gas reduction particles 10 may be used in regions of the world in which there is sufficient water vapor present in the atmosphere to support the photosynthesis.

The photosynthesis thereby generates oxygen and simple carbohydrates such as glucose. The oxygen generated from the photosynthesis would remain in the atmosphere. On the other hand, the simple carbohydrates would precipitate from the atmosphere. In view of the relatively small amounts of the simple carbohydrates that are generated from the photosynthesis, it is not envisioned that the precipitation of the simple carbohydrates would potentially cause any negative affects when landing on the ground, persons, animals or plants. However, if there are potential concerns about the negative effects of the simple carbohydrates on the ground, persons, animals or plants in certain regions, the greenhouse gas reduction particles 10 may not be dispensed proximate to those areas.

As an alternative to using the nano-chloroplasts for photosynthesis, it is possible to use artificial biochemical machinery for photosynthesis. An advantage of the artificial biochemical machinery over the nano-chloroplasts is that the artificial biochemical machinery may be operable over larger ambient conditions such as the low temperatures and low pressures that are experienced at high altitudes.

Similar to the nano-chloroplasts, the artificial biochemical machinery should be on the order of a nano-size to reduce the impact of gravity on the artificial biochemical machinery so that the artificial biochemical machinery remains airborne for an extended period of time.

In particular, there needs to be a balance between the greenhouse gas reduction particles being sufficiently large to fit the biochemical machinery while being sufficiently small to remain airborne for an extended period of time. In many instances, the greenhouse gas reduction particles have a size of between about 100 nanometers and about 1,000 nanometers.

In one such embodiment, the chemical machinery is extracted from bacteria and imprinted onto smaller particles. For example, in certain embodiments, the biochemical machinery in the *Prochlorococcus* bacteria is imprinted onto particles that are smaller than directly using the *Prochlorococcus* bacteria. Through such a process, it is possible to reduce the gravitational impact on the greenhouse gas reduction particles, which enables the greenhouse gas reduction particles to remain airborne for longer periods of time.

The technology used in such a process is similar at a high level to the technology used in conjunction with manufacturing mRNA COVID-19 vaccines, which are true nano-particles having a size of between about 60 nanometers and about 100 nanometers. This technique may include the formation of lipid wrapped particles.

It is envisioned that the reduced size photosynthetic bacteria particles would have a size that is larger than the size of the mRNA vaccine particles. Such particles would likely have a size that is near the nano/micro boundary such as being in the range of 200 nanometers and 500 nanometers.

The greenhouse gas reduction particles 10 may also include a second region 22 that contains hydrocarbon oxidizing nano-organisms. The hydrocarbons that are preferentially oxidized by the nano-organism are the hydrocarbons present in the atmosphere that are referred to as greenhouse gases.

An example of one such hydrocarbon that is referred to as a greenhouse gas is methane. It is recognized that methane is a far more potent greenhouse gas than carbon dioxide. An example of one such hydrocarbon oxidizing bacterium is *Methylococcus capsulatus*.

The methane conversion process may be similar to the carbon dioxide conversion process in which the methane is converted into carbohydrates. In certain embodiments, the methane oxidizing bacteria have a size of around 1 micrometer.

Similar to the nano-chloroplasts, the hydrocarbon oxidizing nano-organisms may be selected to remain active in the ambient conditions in which the greenhouse gas reduction particles are intended to be used. For situations where the greenhouse gas reduction particles are intended to be deployed into the upper atmosphere, the hydrocarbon oxidizing nano-organisms should remain active in to relatively low temperatures that are typically experienced in the upper atmosphere.

Through the consumption of the methane molecules present in the atmosphere, these nano-organisms would remove the methane molecules from the atmosphere. Similar to the carbohydrates produced from the photosynthesis, the carbohydrates produced from the methane would fall to the ground.

As an alternative to using the nano-organisms to oxidize the methane, it is possible to oxidize the methane using artificial biochemical machinery. An advantage of the artificial biochemical machinery over the nano-organisms is that the artificial biochemical machinery may be operable over larger ambient conditions such as the low temperatures and low pressures that are experienced at high altitudes.

Similar to the nano-chloroplasts, the artificial biochemical machinery should be on the order of a nano-size to reduce the impact of gravity on the artificial biochemical machinery so that the artificial biochemical machinery remain airborne for an extended period of time.

It is possible to vary the concentrations of the nano-chloroplasts and the nano-organisms in the greenhouse gas reduction particles 10 depending on whether it is desired to emphasize removal of carbon dioxide or methane from the atmosphere.

The greenhouse gas reduction particles 10 may be deployed in the upper atmosphere. A variety of techniques may be used for deploying the greenhouse gas reduction particles 10 in the upper atmosphere. An example of one technique that may be used for deploying the greenhouse gas reduction particles 10 in the upper atmosphere is a space elevator.

Other options for deploying the greenhouse gas reduction particles 10 in the atmosphere include dispersing the greenhouse gas reduction particles 10 from an airborne vehicle such as an airplane, a helicopter, a rocket or a balloon. Still other options for deploying the greenhouse gas reduction particles 10 include man-made structures such as a building or a natural structure such as a mountain or hill.

It is also possible to use structures such as artificial trees for deploying the greenhouse gas reduction particles 10. In one such configuration, the greenhouse gas reduction particles 10 are placed within the hollow trunk and branches of the artificial trees so that the greenhouse gas reduction particles 10 are periodically released from the twig tips. It is also possible for the greenhouse gas reduction particles 10 to function while the greenhouse gas reduction particles 10 remain associated with the trees.

The process of inoculating the atmosphere may take place over an extended period of time. In certain embodiments, the inoculation may be done over about 6 months. In other embodiments, the inoculation is done as a single event such as when the greenhouse gas reduction particles are discharged from an airplane.

Because of the relatively small size and relatively small weight of the greenhouse gas reduction particles 10, the greenhouse gas reduction particles 10 may remain airborne for an extended period of time. As such, the greenhouse gas reduction particles 10 falling to earth will not pose a problem with the continued action of the greenhouse gas reduction particles 10 removing carbon dioxide and possibly also methane from the atmosphere.

In certain embodiments, a substantial portion of the greenhouse gas reduction particles 10 may remain airborne for more than one year. In other embodiments, the substantial portion of the greenhouse gas reduction particles 10 may remain airborne for between about 2 years and about 3 years.

Nanoparticles having a size of about 100 nanometers can essentially stay airborne indefinitely. In contrast, small microparticles/large nanoparticles of about 500 nanometers would likely settle at a rate of around 1-2 inches per hour. This means that it would take between about 2 years and about 3 years for particles that are inoculated at high altitudes to settle to the ground. This settling rate could be impacted by wind at higher elevations and rain at lower elevations.

Particle having a size of about 1 micrometer could stay airborne for between about 6 months and about 1 year. In the microparticles become trapped in the jet stream, the microparticles would likely stay airborne for a considerably longer time period.

The air movement will progressively cause the greenhouse gas reduction particles 10 to progressively become more dispersed. One particularly influential air movement is the jet stream. The dispersion of the greenhouse gas reduction particles will enhance the following stage of the invention.

The invention may also relate to charging the atmosphere such as using the energy from the sun. Particularly strong energy emissions from the sun are in the form of solar storms. The solar energy emissions are known to go in cycles.

Additionally, the atmosphere may be charged using electrically charged missiles. For example, the missiles may carry a payload that is capable of emitting powerful electromagnetic pulses. These types of payloads are typically referred to as EMP bombs.

The energy from the sun alone or in conjunction with missiles will "charge" and activate particles in the atmosphere. A person of skill in the art will appreciate that other techniques may be used to activate the greenhouse gas reduction particles.

A person of skill in the art will appreciate that other techniques may be used to charge the greenhouse gas reduction particles. These other techniques may directly or indirectly charge the greenhouse gas reduction particles at the desired time.

These charged particles containing the nano-chloroplasts alone or also nano-organisms that have been dispersed around the atmosphere, so that they now become sites of artificial photosynthesis and methane breakdown. This process thereby creates an extremely large number of tiny reaction sites that are floating throughout the atmosphere on which the sunlight is absorbed to catalyze the photosynthetic chemical reaction as well as the bacterial reaction.

If additional energy is required, it is possible to use HAARP (high-frequency active auroral research program) facility to provide an additional energy charge.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the FIGURE(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. An atmospheric greenhouse gas reduction method comprising:

forming particles comprising carbon dioxide conversion material;

inoculating the greenhouse gas reduction particles into the atmosphere, wherein after inoculation, a region of the greenhouse gas reduction particles in which the carbon dioxide conversion material is located is oriented away from earth; and using the carbon dioxide conversion material to convert carbon dioxide in the atmosphere into simple carbohydrates.

2. The atmospheric greenhouse gas reduction method of claim 1, wherein the carbon dioxide conversion material is nano-chloroplasts and wherein the nano-chloroplasts comprise *Prochlorococcus* bacteria.

3. The atmospheric greenhouse gas reduction method of claim 1, wherein the carbon dioxide conversion material has a density that is less than a density of other materials in the greenhouse gas reduction particles.

4. The atmospheric greenhouse gas reduction method of claim 1, wherein the greenhouse gas reduction particles further comprise hydrocarbon oxidizing material and wherein the hydrocarbon oxidizing material has a density that is greater than the density of the carbon dioxide conversion material.

5. The atmospheric greenhouse gas reduction method of claim 1, wherein the greenhouse gas reduction particles remain airborne for greater than at least about one year.

6. The atmospheric greenhouse gas reduction method of claim 1, and further comprising adjusting a concentration of the carbon dioxide conversion material and the hydrocarbon oxidizing material in the greenhouse gas reduction particles to preferentially remove carbon dioxide or hydrocarbons from the atmosphere.

7. The atmospheric greenhouse gas reduction method of claim 1, wherein the carbon dioxide conversion material is activated using sunlight and wherein the greenhouse gas reduction particles are inoculated so that a substantial number of the greenhouse gas reduction particles are in the jet stream.

8. The atmospheric greenhouse gas reduction method of claim 1, wherein the greenhouse gas reduction particles are dispersed from at least one of an airborne vehicle, a man-made structure and a natural structure.

* * * * *